(12) United States Patent
Li et al.

(10) Patent No.: US 10,162,077 B2
(45) Date of Patent: Dec. 25, 2018

(54) METHODS AND SYSTEMS FOR INSPECTING A VEHICLE

(71) Applicants: Tsinghua University, Haidian District, Beijing (CN); Nuctech Company Limited, Haidian District, Beijing (CN)

(72) Inventors: Jianmin Li, Beijing (CN); Lei Zeng, Beijing (CN); Qiang Li, Beijing (CN); Wen Wei, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 15/030,511

(22) PCT Filed: Jul. 24, 2015

(86) PCT No.: PCT/CN2015/085059
§ 371 (c)(1),
(2) Date: Apr. 19, 2016

(87) PCT Pub. No.: WO2016/034022
PCT Pub. Date: Mar. 10, 2016

(65) Prior Publication Data
US 2017/0160426 A1   Jun. 8, 2017

(30) Foreign Application Priority Data

Sep. 2, 2014  (CN) .......................... 2014 1 0443149

(51) Int. Cl.
*G06K 9/62* (2006.01)
*G01V 5/00* (2006.01)
(Continued)

(52) U.S. Cl.
CPC ........... *G01V 5/0016* (2013.01); *G01N 23/04* (2013.01); *G06K 7/10366* (2013.01);
(Continued)

(58) Field of Classification Search
CPC ... B23Q 17/2409; G06T 7/0014; G06T 7/001; G06T 7/0004; G06T 7/0002;
(Continued)

(56) References Cited

U.S. PATENT DOCUMENTS

| 8,155,384 B2 * | 4/2012 | Chew | G01V 5/0008 |
| | | | 382/220 |
| 2005/0088320 A1 * | 4/2005 | Kovach | G07C 5/085 |
| | | | 340/933 |

(Continued)

FOREIGN PATENT DOCUMENTS

| CN | 101162204 A | 4/2008 |
| CN | 103744120 A | 4/2014 |

OTHER PUBLICATIONS

Extended European Search Report for Application No. 15837948.7 dated Mar. 19, 2018 in 8 pages.

*Primary Examiner* — Duy M Dang
(74) *Attorney, Agent, or Firm* — Knobbe, Martens, Olson & Bear, LLP

(57) ABSTRACT

A method for inspecting a vehicle includes acquiring a unique identity number of an insepected vehicle, carrying out X-ray scanning on the inspected vehicle to acquire an X-ray image of the inspected vehicle, retrieving at least one historical inspected image related to the unique identity number from a historical inspection database, determining, based on one template image selection algorithm selected from multiple template image selection algorithms, one of the at least one historical inspected images as a template image, determining a difference region between the X-ray image and the template image, and presenting the difference region to a user.

9 Claims, 3 Drawing Sheets

(51) Int. Cl.
*G01N 23/04* (2018.01)
*G06K 7/10* (2006.01)
*G06K 9/00* (2006.01)

(52) U.S. Cl.
CPC ....... *G06K 9/00624* (2013.01); *G06K 9/6201* (2013.01); *G01N 2223/401* (2013.01); *G01N 2223/408* (2013.01); *G06K 2209/23* (2013.01)

(58) Field of Classification Search
CPC ........... G06T 2207/30108; G06T 2207/30156; G06K 2209/19; G06K 7/10366; G06K 9/6201; G01N 2021/8893; G01N 2021/8887; G01V 5/0016
See application file for complete search history.

(56) References Cited

U.S. PATENT DOCUMENTS

| | | | |
|---|---|---|---|
| 2007/0041612 A1 | 2/2007 | Chen et al. | |
| 2008/0044801 A1 | 2/2008 | Modica et al. | |
| 2008/0095310 A1 | 4/2008 | Edwards et al. | |
| 2008/0136625 A1 | 6/2008 | Chew | |
| 2008/0198967 A1* | 8/2008 | Connelly | G01V 5/0016 378/57 |
| 2009/0279772 A1* | 11/2009 | Sun | G06K 9/6298 382/141 |
| 2009/0290757 A1 | 11/2009 | Mian et al. | |
| 2012/0314974 A1* | 12/2012 | Yang | G06K 9/6211 382/294 |

* cited by examiner

METHODS AND SYSTEMS FOR INSPECTING A VEHICLE

CROSS-REFERENCE TO RELATED APPLICATIONS

This application is the U.S. National Phase under 35. U.S.C. § 371 of International Application PCT/CN2015/085059, filed Jul. 24, 2015, which claims priority to Chinese Patent Application No. 201410443149.7, filed Sep. 2, 2014. The disclosures of the above-described applications are hereby incorporated by reference in their entirety

TECHNICAL FIELD

The embodiments of the present disclosure generally relate to radiation inspection, and in particular, to methods and systems for inspecting a vehicle.

BACKGROUND

X-ray radiation imaging is an important approach to inspect security of various vehicles. After a vehicle passes through an X-ray radiation imaging system and an image of the vehicle is generated by the X-ray radiation imaging system, a human inspector may determine whether there are prohibited goods carried secretly in the inspected vehicle by viewing and analyzing the X-ray scanning image, so as to achieve the purpose of security inspection.

In practical security inspection scenarios, it is very difficult for a human inspector to find small goods which are carried secretly in a vehicle by merely viewing an X-ray scanning image of the vehicle with naked eyes. Therefore, there is a need to develop a technology of vehicle inspection to find goods concealed in a vehicle.

SUMMARY

In view of one or more problems in the related art, methods and systems for inspecting a vehicle are proposed.

In an aspect of the present disclosure, a method for inspecting a vehicle is proposed. The method comprises steps of: acquiring a unique identity number of an inspected vehicle; carrying out X-ray scanning on the inspected vehicle, to acquire an X-ray image of the inspected vehicle; retrieving at least one historical inspected image related to the unique identity number from a historical inspection database; determining, based on one template image selection algorithm selected from multiple template image selection algorithms, one of the at least one historical inspected image as a template image; determining a difference region between the X-ray image and the template image; and presenting the difference region to a user.

According to some embodiments, the method further comprises steps of: storing the unique identity number in a historical database in association with the X-ray image.

According to some embodiments, the step of determining a difference region between the X-ray image and the template image comprises:

registering the X-ray image with the template image; and calculating a difference between the X-ray image and the template image which are registered.

According to some embodiments, the step of presenting the difference region to a user comprises: highlighting the difference region in the X-ray image, or displaying the difference region in the X-ray image and displaying no difference region in the X-ray image in an alternative manner at a certain frequency.

According to some embodiments, the multiple template image selection algorithms are selected from the following image processing algorithms: an average grey minimum method, a closest time method, a grey means square error minimum method, a local template method, and a probability template method.

According to some embodiments, the X-ray image of the vehicle is aligned with the template image by using a rigid registration algorithm, solid deformation is reduced by using an elastic registration algorithm, and then a difference image between the two images is post-processed.

In another aspect of the present disclosure, a system for inspecting a vehicle is proposed. The system comprises: an identity (ID) acquisition unit configured to acquire a unique identity number of an inspected vehicle; a radiation imaging system configured to carry out X-ray scanning on the inspected vehicle, to acquire an X-ray image of the inspected vehicle; a storage device configured to store the X-ray image and a historical inspection database; an image processing unit configured to retrieve at least one historical inspected image related to the unique identity number from the historical inspection database, determine, based on one template image selection algorithm selected from multiple template image selection algorithms, one of the at least one historical inspected image as a template image, and determine a difference region between the X-ray image and the template image; and a display device configured to present the difference region to a user.

According to some embodiments, the ID acquisition unit comprises: a camera configured to capture a plate number image of the inspected vehicle; and an identification unit configured to identify a plate number of the inspected vehicle from the plate number image.

According to some embodiments, the ID acquisition unit comprises: a reader configured to read an ID of the inspected vehicle from a radio frequency tag carried by the inspected vehicle.

According to some embodiments, the display device is configured to highlight the difference region in the X-ray image, or display the difference region in the X-ray image and display no difference region in the X-ray image in an alternative manner at a certain frequency.

With the above solutions, different template image selection algorithms are used for different practical security inspection scenarios, which ensures that an optimal template contrast image can be selected to the maximum extent according to requirements of different security inspection sites, thereby ensuring the effects of security inspection by using a subtraction algorithm.

BRIEF DESCRIPTION OF THE DRAWINGS

For better understanding the present disclosure, the present disclosure will be described in detail below in conjunction with accompanying drawings.

DETAILED DESCRIPTION

Figure 1:
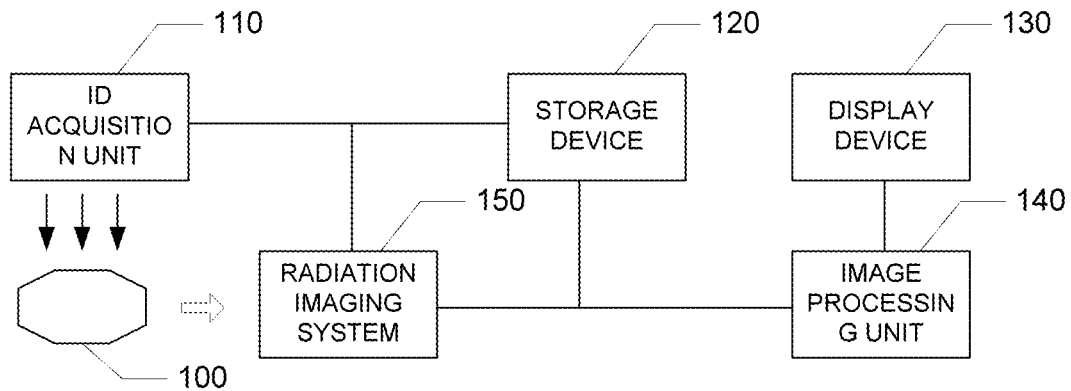
FIG. 1 is a schematic structural diagram of a system for inspecting a vehicle according to an embodiment of the present disclosure.

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the term "and/or" used herein means any and all combinations of one or more listed items.

Contrast analysis is implemented on X-ray scanning images of a vehicle when the vehicle passes through different security inspection sites to inspect a difference therebetween, and thus find goods which are carried secretly in the vehicle. For example, contrast analysis is implemented on a scanning image of a vehicle and a scanning image of an empty vehicle corresponding to the same vehicle. However, there is a need to create an empty vehicle template library, that is, there is a need to obtain an X-ray image by scanning an empty vehicle corresponding to a vehicle which passes through a security inspection site, and store a plate number in an empty vehicle template library in association with the scanning image. A subtraction process is carried out on a scanning image of the vehicle and the scanning image of the empty vehicle corresponding to the vehicle, which is easier to find a difference between the two images, so as to identify goods which are carried secretly.

In order to achieve more effective inspection, in some embodiments, a historical image database is used as an image template library, to solve the problem of creation of an empty vehicle template library. In addition, different algorithms may further be used for specific practical application scenarios, to select an optimal image contrast template according to a suitable one of several algorithms for selecting a template image, so as to carry out contrast analysis on the optimal image contrast template and a scanning image, and calculate a difference between two images by using a subtraction algorithm, and display the difference to a user on a display terminal, thereby achieving the optimal effects of inspection.

In a method for inspecting a vehicle according to some embodiments, a unique identity (ID) of an inspected vehicle is acquired, and then X-ray scanning is carried out on the inspected vehicle, to acquire an X-ray image of the inspected vehicle. At least one historical inspected image related to the unique ID is retrieved from a historical inspection database. One of the at least one historical inspected image is determined as a template image based on one template image selection algorithm selected from multiple template image selection algorithms. A difference region between the X-ray image and the template image is determined and presented to a user. With the above solutions, different template image selection algorithms are used for respective practical security inspection scenarios, and thus this ensures that an optimal template contrast image can be selected to the maximum extent according to requirements of different security inspection sites, thereby ensures the effects of security inspection by using a subtraction algorithm.

According to some embodiments, a suitable algorithm may be selected from an average grey minimum method, a closest time method, a grey means square error minimum method, a local template method, and a probability template method or the like.

1) Average Grey Minimum Method (also Referred to as an Average Grey Minimum Value Algorithm)

All pixels in an image are traversed to acquire and accumulate grey values, and divide the accumulated grey value by a number of pixels. An image with a minimal value which is acquired by using the algorithm is used as an image contrast template. The value being minimal represents that there are least goods carried secretly in the image, and the image is substantially equivalent to a scanning image of an empty vehicle.

2) Closest Time Method

A scanning image which is obtained at a time when the vehicle passes through a security inspection site closest to a time when the vehicle is currently scanned is selected from a historical template library as an image contrast template. The algorithm is generally applied to security inspection of a transit vehicle, so as to compare images to determine whether there are added goods which are carried secretly between two transits.

3) Grey Means Square Error Minimum Method

Various template images are selected in turn from a historical template library. Assuming that a template image which is currently selected is X, and an image which is being inspected is Y. Then, various pixel values of X and Y are traversed to obtain difference values there-between, then square the difference values, and finally sum the squared difference values of all pixels. The same algorithm is applied to each template image, and then a template image with a minimum sum is selected.

4) Local Template Method

The local template method is to divide an image to be inspected and template images into multiple regions respectively, and selection of each template region is determined by using "a grey means square error minimum method."A template image which is generated in such a way is stored in a memory, and is merely effective for a current inspected image. It needs to recalculate a template image for a subsequent inspected image.

5) Probability Template Method

The probability template method needs to create a data model according to images in a historical library, and therefore, this algorithm requires the historical database to have a certain number of historical images (more than 100 images) as a basis. An algorithm for model creation is described as follows:

100 images are selected randomly from a historical image library, and values of pixels in the same position are traversed in turn to calculate an average value p and a variance a, so as to obtain an interval range (p−2.5a, p+2.5a) of grey values for each pixel. When grey values of pixels in the same position are within this interval, it is considered that the pixels comply with the model. The constant 2.5 is not a fixed value, and may be adjusted according to specific scenarios. The model created by using this algorithm may be stored, unless new template images are selected for recalculation.

FIG. 1 is a schematic structural diagram of a system for inspecting a vehicle according to an embodiment of the present disclosure. As shown in FIG. 1, the system for inspecting a vehicle according to the embodiment of the present disclosure relates to a technology of security inspection by using X-ray radiation imaging, particularly a technology of automatic selection of an optimal template image for contrast detection in a technology of automatic detection of goods which are carried secretly in a vehicle.

The system illustrated in FIG. 1 includes an ID acquisition unit 110, a radiation imaging system 150, a storage device 120, an image processing unit 140 and a display device 130.

In some embodiments, the ID acquisition unit 110 acquires a unique ID number of an inspected vehicle. For example, the ID acquisition unit 110 may include a camera configured to capture a plate number image of the inspected vehicle; and an identification unit configured to identify a plate number of the inspected vehicle from the plate number image. In other embodiments, the ID acquisition unit 110 may include a reader configured to read an ID of the inspected vehicle from a radio frequency (RF) tag carried by the inspected vehicle.

The radiation imaging system 150 carries out X-ray scanning on the inspected vehicle to obtain an X-ray image of the inspected vehicle. The storage device 120 stores the X-ray image and a historical inspection database.

The image processing unit 140 retrieves at least one historical inspected image related to the unique ID number from the historical inspection database, determines, based on one template image selection algorithm selected from multiple template image selection algorithms, one of the at least one historical inspected image as a template image, and determines a difference region between the X-ray image and the template image. The display device 130 presents the difference region to a user.

For example, when a vehicle needs to pass through a security inspection site, the ID acquisition unit 110 may identify the corresponding vehicle through a vehicle identification unit to generate a unique ID of the vehicle through a software system, for example, a plate number. The unique ID of the vehicle in the software system is a unique ID of the vehicle when the vehicle passes through the security inspection site. The ID may be generated by the software system for the vehicle, or may also be generated by identifying a plate number of the vehicle. Currently, the software system may identify the vehicle by using a plate number.

After the software system acquires the unique ID (for example, a plate number) of the vehicle through the vehicle identification unit, the radiation imaging system 150 may carry out X-ray scanning on the vehicle, and generate an X-ray scanning image of the vehicle by using a corresponding processing algorithm. After the X-ray scanning image is generated, the X-ray scanning image is associated with the unique ID of the vehicle, and is transmitted to the display device 150 for display. After the vehicle is inspected, the data (including the X-ray image, the ID information) is written into a historical database. If the software system is used to identify the vehicle when the vehicle is to pass through a security inspection site the next time, the data may be used as a template contrast image.

The image processing unit 140 is responsible for retrieving, from a template contrast image library (i.e., a historical image library), all of historical records having the same unique ID (a plate number) as that of the vehicle to be inspected, and processing each image by using a corresponding image processing algorithm (i.e., a template image selection algorithm), to select an optimal template image corresponding to the algorithm. For example, if an average grey minimum method is chosen, all images in the retrieved result are processed by using the average grey minimum method, to select an image with a minimal average grey value as a template contrast image. In terms of the average grey minimum method, an image with a minimal average grey value of the images in the retrieved result is the optimal template contrast image. An input of the retrieval module is an ID number of the vehicle to be inspected, and an output of the retrieval module is an optimal template image (a historical image) which has the same ID and complies with a certain image algorithm.

In addition, the image processing unit 140 may carry out a subtraction algorithm. For example, an image to be inspected is registered with the template image by using a characteristic point alignment method, and then a difference between two images is calculated by using a difference detection method. A region with a large difference is a region where goods which are carried secretly are located. An input of the subtraction algorithm is data of an image to be inspected of the vehicle and data of the retrieved optimal template image having the same vehicle ID. An output of the subtraction algorithm is data of a difference region between two images. The display module draws an outline of the difference region on the image to be inspected by using lines with a certain color according to the data of the difference region.

The display device 130 is configured to display the X-ray scanning image, and is further configured to display the difference region between the image to be inspected and the optimal template image after the subtraction algorithm is implemented. Generally, an outline of the difference region is marked on the image to be inspected by using lines with a certain color, to prompt a human inspector that there are goods which are carried secretly in this difference region, so as to achieve better effects of contrast prompt for security inspection.

With the above description of the system, a general process for security inspection of a vehicle may be as follows. The vehicle passes through a security inspection site. The vehicle is identified to generate a unique ID number. An X-ray radiation imaging system scans the vehicle to generate an X-ray scanning image. The unique ID number of the vehicle is associated with the X-ray scanning image (i.e., an X-ray image). A criterion of a vehicle retrieval algorithm and the unique ID of the vehicle are acquired. Retrieval is carried out in the historical library to acquire an optimal template image. A subtraction algorithm is carried out to acquire a difference region between the image to be inspected and the template image. The difference region is presented through a display module. The vehicle leaves the security inspection site. The whole security inspection process ends, and the image to be inspected is written into a historical database.

In other embodiments, the above process may be simplified as follows. The vehicle passes through a security inspection site. The vehicle is identified to generate a unique ID number. An X-ray radiation imaging system scans the vehicle to generate an X-ray scanning image. The unique ID number of the vehicle is associated with the X-ray scanning image. The X-ray scanning image is displayed through a display module. A human inspector manually inspects the image to determine whether there are goods which are carried secretly in the vehicle. The vehicle leaves the security inspection site. The whole security inspection process ends, and the image to be inspected is written into a historical database.

Figure 2:
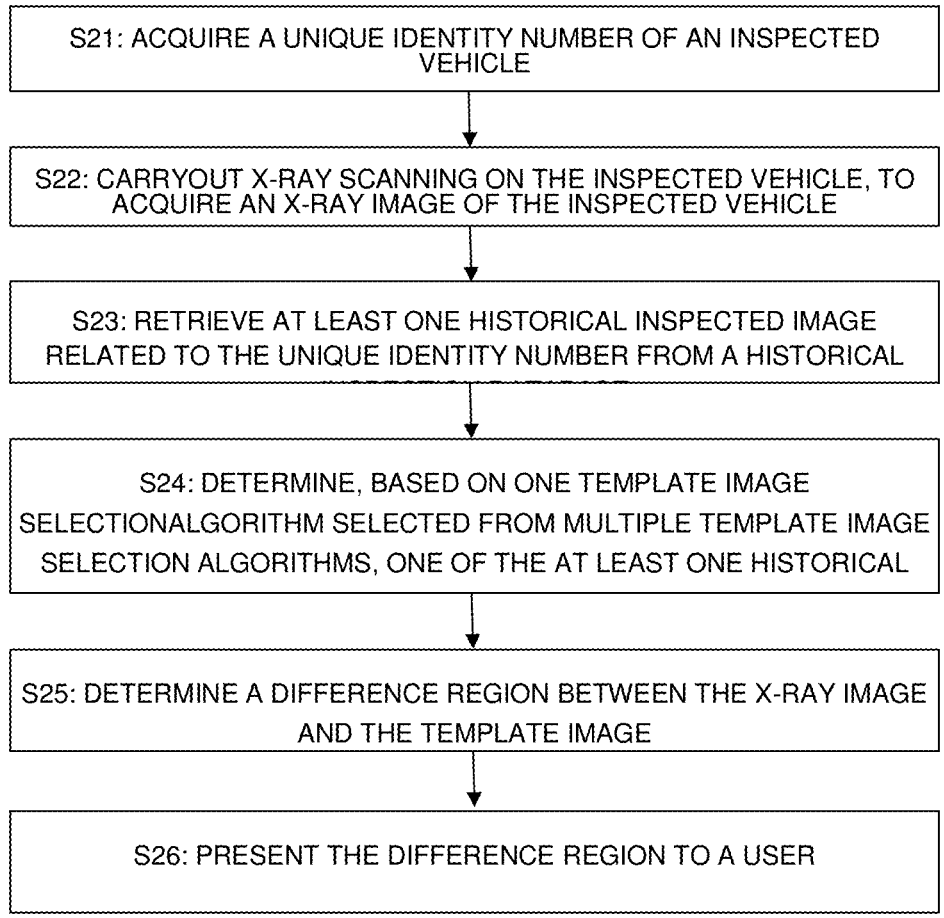
FIG. 2 is a schematic flowchart of a method for inspecting a vehicle according to an embodiment of the present disclosure.

FIG. 2 is a schematic flowchart of a method for inspecting a vehicle according to an embodiment of the present disclosure. As shown in FIG. 2, in step S21, a unique ID number of the vehicle to be inspected is acquired. For example, the unique ID number of the vehicle is acquired by using a camera and identification software, or the unique ID number of the vehicle is acquired by using Radio Frequency Identification (RFID), for example, a plate number of the vehicle. In other embodiments, other ID numbers may also be used, for example, a frame number or the like.

In step S22, X-ray scanning is carried out on the inspected vehicle to acquire an X-ray image of the inspected vehicle. For example, transmission scanning is carried out on the vehicle through an X-ray radiation imaging system to acquire a transmission image.

In step S23, at least one historical inspected image related to the unique ID number is retrieved from a historical inspection database. For example, one image is selected from historical images of the vehicle.

In step S24, one of the at least one historical inspected images is determined as a template image based on one template image selection algorithm selected from the multiple template image selection algorithms. Then, a difference region between the X-ray image and the template image is determined in step S25 and is presented to a user in step S26.

Figure 3:
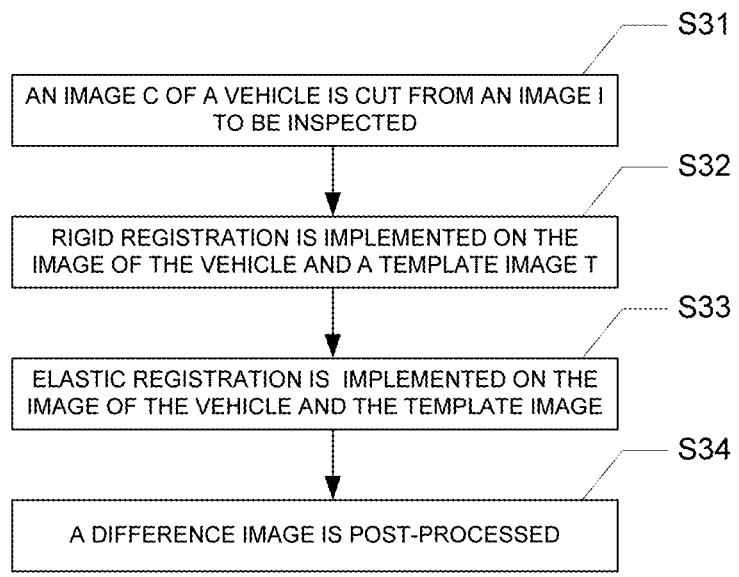
FIG. 3 is a schematic diagram of a subtraction process used in the systems and methods for inspecting a vehicle according to the embodiments of the present disclosure.

FIG. 3 is a schematic diagram of a subtraction process used in the systems and methods for inspecting a vehicle according to the embodiments of the present disclosure. As shown in FIG. 3, in step S31, an image C of the vehicle is cut from an image I to be inspected. Then, in step S32, assuming that a noise is within a certain range, the images are aligned by using rigid registration. Further, in step S33, the influence of solid deformation is reduced by using elastic registration. Then, in step S34, a difference image is post-processed, to classify goods which are carried secretly, articles, and goods which are detected falsely due to solid deformation, scanning noises or the like, and finally represent the goods which are carried secretly in a result.

Thus, a normal scanning image of a vehicle is used as an inspection template image of the same vehicle later, which basically solves the problem of difficulty in creation of a template library. In addition, an automatic template image selection and association algorithm is used to select an optimal template image for matching to the maximum extent, which better ensures the effects of image contrast. Many image algorithms can be used as a template image selection algorithm, which can adapt to the practical application scenarios of security inspection to the maximum extent.

The example of the system according to the present disclosure will be described by taking security inspection of a vehicle as an example. Assuming that the system uses a plate number as a unique identity tag of the vehicle, i.e., a unique ID, and the plate number has been stored in a historical template library (i.e., a template image library), the implementations are achieved in the following steps.

Figure 4:
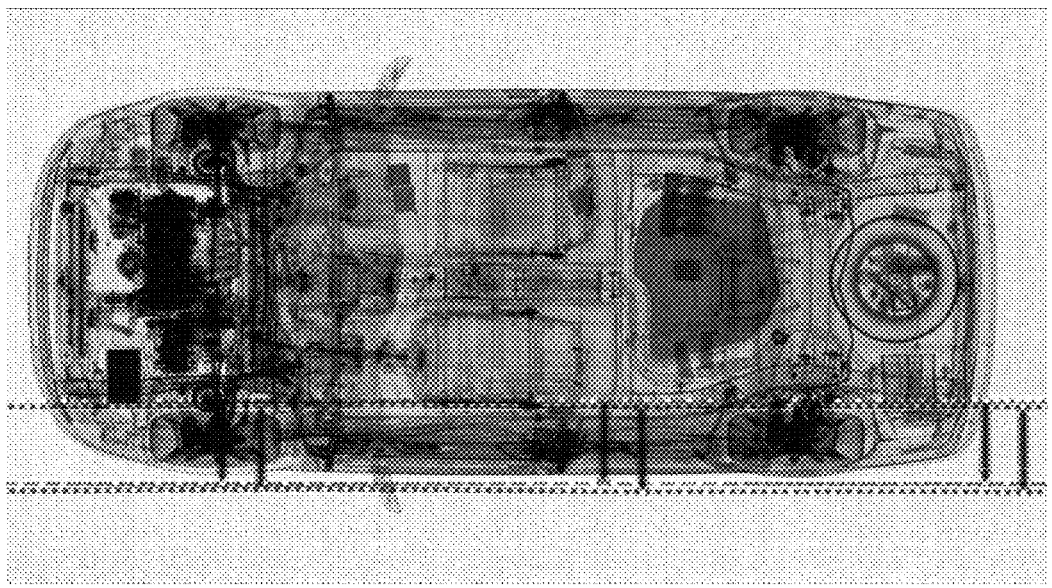
FIG. 4 is a schematic diagram of an image to be inspected.

The vehicle passes through a security inspection site. And an identification module of a software system may identify that a unique ID of the vehicle is "京N8888".Then, an X-ray radiation imaging system may scan the vehicle to generate a scanning image of the vehicle to be inspected, as shown in FIG. 4, and the scanning image is associated with the unique ID of the vehicle.

Then, the identified unique ID of the vehicle, i.e., "京N88888" is acquired, and a vehicle retrieval algorithm is selected. In this example, "an average grey minimum method" is selected in conjunction with a practical security inspection scenario. The description of the algorithm is described in the background. The selected algorithms may be different for different practical requirements of security inspection. For example, in a case of transit, "a closest time method" is selected to select a scanning image which is closest in time from the historical records.

Figure 5:
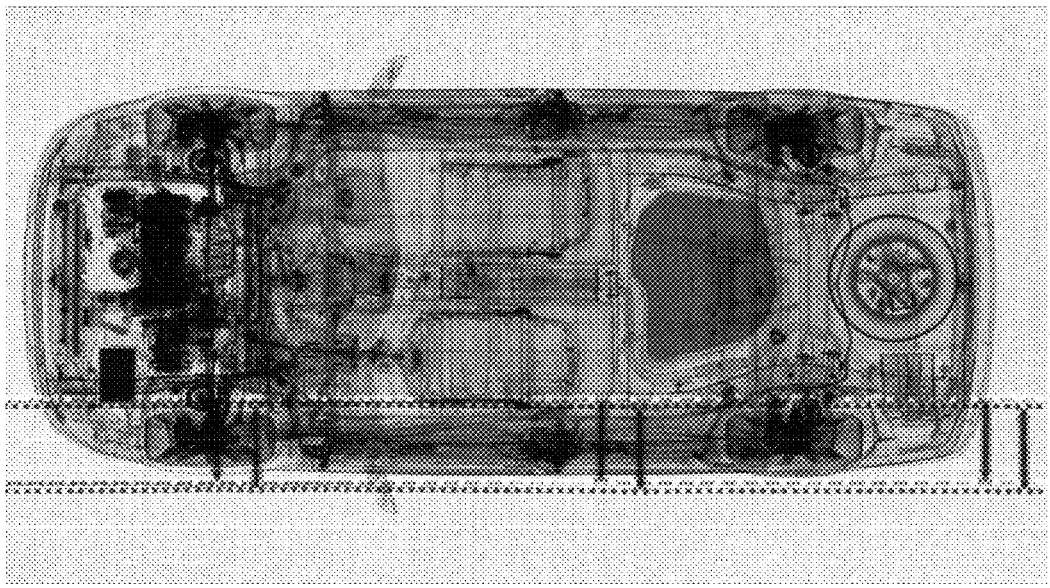
FIG. 5 is a schematic diagram of a template image selected in the systems and methods according to the embodiments of the present disclosure.

Historical records having the same plate number are searched from the historical image library according to the unique ID of the vehicle, i.e., "京N88888". These records are all historical records of the vehicle to be inspected when the vehicle passes through security inspection sites. The above search history records are traversed to acquire a historical image of each record, an average grey value of the image is calculated by using "an average grey minimum value method", and an image with a minimal average grey value is recorded. After the records are traversed completely, the image with a minimal average grey value is returned as a template image, as shown in FIG. 5.

The original data of the image to be inspected and the original data of the above returned image are transferred to a subtraction algorithm. A difference between the two images is calculated by using the subtraction algorithm, and data of the difference region is returned to an invoker.

Figure 6:
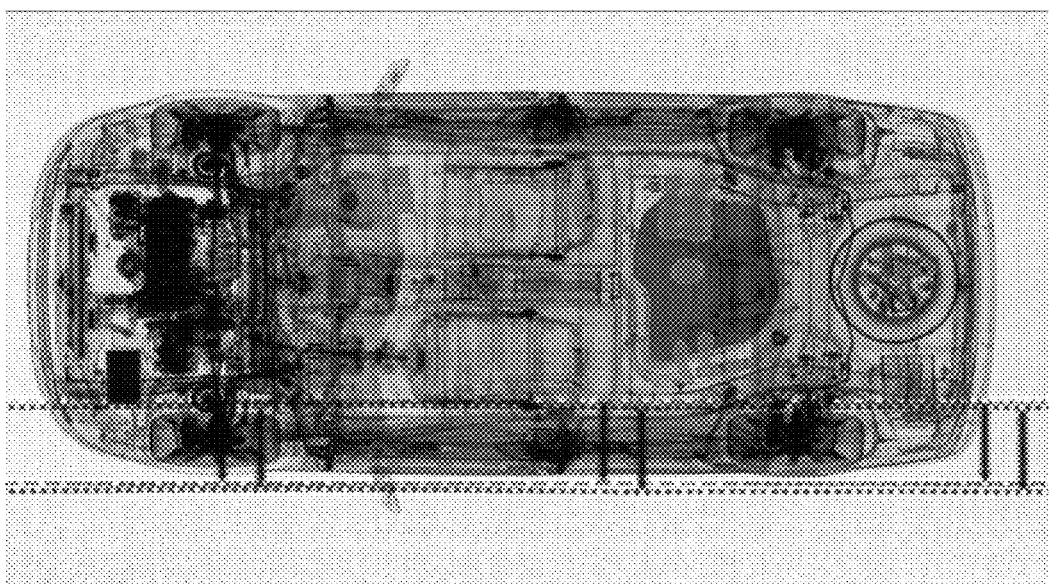
FIG. 6 is a schematic diagram illustrating an image to be inspected with a difference region overlapped thereon.

The image device 130 may use the returned data of the difference region for display, and present the difference region to a human inspector by using lines with a certain color, as shown in FIG. 6. The presentation of these difference regions represent parts of the inspected vehicle where there may be goods which are carried secretly. The human inspector may determine whether there are goods which are carried secretly according to the displayed difference regions.

The vehicle exits the security inspection site, which indicates that the whole process of the software system for the inspected vehicle ends. The inspected image and the conclusion information are written into a historical database.

According to the above embodiments, the problem of difficulty in creation of an image template library is solved. In addition, the problem of selection of an optimal template image may also solved, which ensures the effects of the X-ray scanning image contrast, and improves the quality of security inspection. In addition, the problem of association of a vehicle with a scanning image is solved, and a unique ID of the vehicle is associated with previous scanning images. For query of previous records of a certain vehicle, previous scanning images of the vehicle are queried according to the unique ID of the vehicle, and categories of the previous records are displayed. In the related art, an image in an empty vehicle template library are used as a template image, but in some practical application scenarios, it is not an optimal selection to use an X-ray scanning image of an empty vehicle as a template image, particularly for a transit vehicle. An optimal template image of the transit vehicle is an X-ray scanning image of the vehicle when the vehicle passes through a security inspection site last time.

The foregoing detailed description has set forth various embodiments of the methods and systems for inspecting a vehicle via the use of diagrams, flowcharts, and/or examples. In a case that such diagrams, flowcharts, and/or examples contain one or more functions and/or operations, it will be understood by those skilled in the art that each function and/or operation within such diagrams, flowcharts or examples may be implemented, individually and/or collectively, by a wide range of structures, hardware, software, firmware, or virtually any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

While the present disclosure has been described with reference to several typical embodiments, it is apparent to those skilled in the art that the terms are used for illustration and explanation purpose and not for limitation. The present disclosure may be practiced in various forms without departing from the spirit or essence of the present disclosure. It should be understood that the embodiments are not limited to any of the foregoing details, and shall be interpreted broadly within the spirit and scope as defined by the following claims. Therefore, all of modifications and alternatives falling within the scope of the claims or equivalents thereof are to be encompassed by the claims as attached.

We claim:

1. A method for inspecting a vehicle, comprising steps of:
    acquiring a unique identity number of an inspected vehicle;
    carrying out X-ray scanning on the inspected vehicle to acquire an X-ray image of the inspected vehicle;
    retrieving at least one historical inspected image related to the unique identity number from a historical inspection database;
    determining, based on one template image selection algorithm selected from multiple template image selection algorithms, one of the at least one historical inspected image as a template image;
    determining a difference region between the X-ray image and the template image;
    presenting the difference region to a user, and
    wherein the multiple template image selection algorithms are selected from the following image processing algorithms: an average grey minimum method, a closest time method, a grey means square error minimum method, a local template method, and a probability template method.

2. The method according to claim 1, wherein the step of determining a difference region between the X-ray image and the template image comprises:
    registering the X-ray image with the template image; and
    calculating a difference between the X-ray image and the template image which are registered.

3. The method according to claim 1, wherein the step of presenting the difference region to a user comprises:
    highlighting the difference region in the X-ray image.

4. The method according to claim 1, wherein the X-ray image of the vehicle is aligned with the template image by using a rigid registration algorithm, solid deformation is reduced by using an elastic registration algorithm, and then a difference image between the two images is post-processed.

5. The method according to claim 1, further comprising steps of:
    storing the unique identity number in a historical database in association with the X-ray image.

6. A system for inspecting a vehicle, comprising:
    an identity (ID) acquisition unit configured to acquire a unique identity number of an inspected vehicle;
    a radiation imaging system configured to carry out X-ray scanning on the inspected vehicle, to acquire an X-ray image of the inspected vehicle;
    a storage device configured to store the X-ray image and a historical inspection database;
    an image processing unit configured to retrieve at least one historical inspected image related to the unique identity number from the historical inspection database, determine, based on one template image selection algorithm selected from multiple template image selection algorithms, one of the at least one historical inspected image as a template image, and determine a difference region between the X-ray image and the template image; and
    a display device configured to present the difference region to a user,
    wherein the multiple template image selection algorithms are selected from the following image processing algorithms: an average grey minimum method, a closest time method, a grey means square error minimum method, a local template method, and a probability template method.

7. The system according to claim 6, wherein the ID acquisition unit comprises:
    a camera configured to capture a plate number image of the inspected vehicle; and
    an identification unit configured to identify a plate number of the inspected vehicle from the plate number image.

8. The system according to claim 6, wherein the ID acquisition unit comprises:
    a reader configured to read the ID of the inspected vehicle from a radio frequency tag carried by the inspected vehicle.

9. The system according to claim 6, wherein the display device is configured to highlight the difference region in the X-ray image, or display the difference region in the X-ray image and display no difference region in the X-ray image in an alternative manner at a certain frequency.

* * * * *